United States Patent
Pedicini

(10) Patent No.: US 9,901,354 B2
(45) Date of Patent: Feb. 27, 2018

(54) ELECTRIC MOTOR DRIVEN TOOL FOR ORTHOPEDIC IMPACTING

(71) Applicant: Medical Enterprises, LLC, Nashville, TN (US)

(72) Inventor: Christopher Pedicini, Nashville, TN (US)

(73) Assignee: Medical Enterprises, LLC, Norcross, GA (US)

( * ) Notice: Subject to any disclaimer, the term of this patent is extended or adjusted under 35 U.S.C. 154(b) by 960 days.

(21) Appl. No.: 14/250,102

(22) Filed: Apr. 10, 2014

(65) Prior Publication Data

US 2015/0289887 A1    Oct. 15, 2015
US 2017/0172584 A9    Jun. 22, 2017

Related U.S. Application Data

(62) Division of application No. 12/980,329, filed on Dec. 29, 2010, now Pat. No. 8,695,726.

(51) Int. Cl.
*A61B 17/92* (2006.01)
*A61B 17/16* (2006.01)
*A61B 90/30* (2016.01)

(52) U.S. Cl.
CPC ...... *A61B 17/1628* (2013.01); *A61B 17/1604* (2013.01); *A61B 17/1626* (2013.01); *A61B 17/1659* (2013.01); *A61B 17/92* (2013.01); *A61B 17/1668* (2013.01); *A61B 2017/922* (2013.01); *A61B 2090/309* (2016.02)

(58) Field of Classification Search
CPC ............ A61B 17/1628; A61B 17/1604; A61B 17/1626; A61B 17/92; A61B 17/1668; A61B 2017/922; A61B 2090/309

USPC ............... 173/204, 200, 48; 227/175.1
See application file for complete search history.

(56) References Cited

U.S. PATENT DOCUMENTS

| | | | | |
|---|---|---|---|---|
| 1,920,765 A | * | 8/1933 | Rasch | B25D 9/10 123/46 R |
| 5,057,112 A | * | 10/1991 | Sherman | A61B 17/1604 606/100 |
| 5,108,400 A | * | 4/1992 | Appel | A61B 17/1659 173/91 |
| 5,145,369 A | | 9/1992 | Lustig et al. | |

(Continued)

FOREIGN PATENT DOCUMENTS

WO    WO 2012/092387 A2    7/2012

OTHER PUBLICATIONS

Office Action dated May 24, 2016 in Japanese Patent Application No. 2013-547652 (with English language translation).

*Primary Examiner* — Michelle Lopez
(74) *Attorney, Agent, or Firm* — Gardella Grace P.A.

(57) ABSTRACT

An orthopedic impacting tool comprises a motor, a linear motion converter, an air chamber, a compression piston, an impacting element, an anvil element, and a broach adapter. The compression piston may cause the impacting element to apply controlled force on a broach adapter to create a precise opening for subsequently disposing a prosthesis in a patient. The tool allows forward or backward impacting for expanding the size or volume of the opening or for facilitating removal of the broach and tool from the opening. A force adjustment control of the tool allows a user to increase or decrease the impact force. A light source and hand grips improve ease of operation of the tool.

10 Claims, 6 Drawing Sheets

(56) References Cited

U.S. PATENT DOCUMENTS

| | | | |
|---|---|---|---|
| 5,163,519 A * | 11/1992 | Mead ..................... | B25C 11/00 173/135 |
| 5,984,027 A * | 11/1999 | Kato ..................... | B25D 11/125 173/200 |
| 6,264,660 B1 * | 7/2001 | Schmidt ............. | A61B 17/8847 606/100 |
| 6,520,266 B2 * | 2/2003 | Bongers-Ambrosius ............ | B25D 11/12 173/115 |
| 6,899,715 B1 | 5/2005 | Beaty | |
| 7,001,393 B2 | 2/2006 | Schwenke et al. | |
| 8,393,409 B2 * | 3/2013 | Pedicini ................. | A61B 17/92 173/109 |
| 8,602,124 B2 * | 12/2013 | Pedicini ................. | B25D 17/00 173/109 |
| 8,636,647 B2 * | 1/2014 | Silvestrini ............. | A61F 9/0017 600/104 |
| 8,695,726 B2 * | 4/2014 | Pedicini ............. | A61B 17/1604 173/109 |
| 8,936,105 B2 * | 1/2015 | Pedicini ............. | A61B 17/1604 173/114 |
| 8,936,106 B2 * | 1/2015 | Pedicini ............. | A61B 17/1626 173/109 |
| 2008/0234711 A1 | 9/2008 | Houser et al. | |
| 2012/0172939 A1 * | 7/2012 | Pedicini ............. | A61B 17/1604 606/86 R |
| 2012/0215267 A1 * | 8/2012 | Pedicini ................. | A61B 17/92 606/86 R |
| 2013/0161050 A1 * | 6/2013 | Pedicini ................. | B25D 17/00 173/201 |
| 2014/0318819 A1 * | 10/2014 | Pedicini ............. | A61B 17/1626 173/2 |
| 2014/0318823 A1 * | 10/2014 | Pedicini ............. | A61B 17/1604 173/201 |

* cited by examiner

ELECTRIC MOTOR DRIVEN TOOL FOR ORTHOPEDIC IMPACTING

CROSS REFERENCE TO RELATED APPLICATIONS

The present application is a divisional application of pending U.S. patent application Ser. No. 12/980,329, filed on Dec. 29, 2010, the disclosure of which is incorporated by reference.

FIELD

The present disclosure relates to electric tools for impacting in orthopedic applications, and, more particularly, to an electric motor driven tool for orthopedic impacting that is capable of providing controlled impacts to a broach, chisel, or other device for creating an opening in an area (in a bone structure, for example) to securely receive prosthesis within the area.

In the field of orthopedics, prosthetic devices such as artificial joints, are often implanted or seated in a patient's body by seating the prosthetic device in a cavity of a bone of the patient. The cavity must be created before the prosthesis is seated or implanted, and traditionally, a physician may remove worn, excess, or diseased bone structure from the area in which the cavity will be formed, and then drill and hollow out a cavity along the medullar canal of the bone. A prosthesis usually includes a stein or other protrusion that serves as the particular portion of the prosthesis that is inserted into the cavity.

To create such a cavity, a physician may use a broach, which broach conforms to the shape of the stem of the prosthesis. Solutions known in the art include providing a handle with the broach, which handle the physician may grasp while hammering the broach into the implant area. Unfortunately, this approach is clumsy and unpredictable as being subject to the skill of the particular physician. This approach almost will always inevitably result in inaccuracies in the location and configuration of the cavity. Further, this approach carries with it the risk that the physician will damage bone structure in unintended areas.

Another technique for creating the prosthetic cavity is to drive the broach pneumatically, that is, by compressed air. This approach is disadvantageous in that it prevents portability of an impacting tool, for instance, because of the presence of a tethering air line, air being exhausted from a tool into the sterile operating field and fatigue of the physician operating the tool. Further this approach, as exemplified in U.S. Pat. No. 5,057,112 does not allow for precise control of the impact force or frequency and instead functions very much like a jackhammer when actuated. Again, this lack of any measure of precise control makes accurate broaching of the cavity more difficult.

Another disadvantage of tools known in the art is the accumulation of fluids, such as body fluids or moisture, on handgrips of such tools during prolonged periods of use. For example, difficulty of operation of a broach impacting device known in the art may increase during a surgical procedure as handgrips may become saturated with bodily fluids and thus the physician's hold on such a prior art device may become impaired.

Consequently, there exists a need for an impacting tool that overcomes the various disadvantages in the prior art.

In view of the foregoing disadvantages of the prior art, an electric motor-driven orthopedic impacting tool configured to include all the advantages of the prior art, and to overcome the drawbacks inherent therein is provided. The tool may be used by orthopedic surgeons for orthopedic impacting in for example hips, knees, and shoulders. The tool is capable of holding a broach, chisel, or other device and gently tapping the broach, chisel or other device into the cavity with controlled percussive impacts, resulting in a better fit for the prosthesis or the implant. Further, the control afforded by such an electrically manipulated broach, chisel, or other device allows adjustment of the impact settings according to a particular bone type or other profile of a patient. The tool additionally enables proper seating or removal of the prosthesis or the implant into or out of an implant cavity.

In an embodiment, an electric motor-driven orthopedic impacting tool comprises a control unit, a housing, a linear motion converter, at least one reducing gear, an impacting element (also referred to herein as a striker), an air chamber, as compression piston, and a force adjustment control means (hereinafter referred to as 'control means'). The tool may further include a motor, an LED, a handle portion with at least one handgrip for comfortable gripping the tool, a broach adapter, as battery, a feedback system and a nosepiece for the broach adapter. At least some of the various components are preferably contained within the housing. The tool is capable of applying cyclic impact forces on a broach, chisel, or other device, or an implant and of finely tuning impact force to a plurality of levels of impact force.

In an embodiment, the tool further comprises a control means, which means includes a force adjustment element, and which element may control the impact force and avoid damage caused by uncontrolled impacts.

The tool further comprises an anvil element, which anvil element includes both a forward and rearward point of impact and a guide that constrains the striker to move in a substantially axial direction. In operation, the movement of the striker along the guide of the anvil element continues in either a forward, or rearward direction until the striker hits the point of impact. As used in this context, "forward direction" connotes movement of the striker toward a broach or patient, and "rearward direction" connotes movement of the striker away from the broach or chisel or patient. If the impact point is at the front of the tool, i.e., in a forward direction, the impact causes the percussive force to be transmitted to a broach or chisel, pushing it further into the cavity. If the impact point is at the rear of the tool, the percussive force tends to pull the broach or chisel out of the cavity. The selectivity of either bidirectional or unidirectional impacting provides flexibility to a surgeon in either cutting or compressing material within the implant cavity, in that the choice of material removal or material compaction is often a critical decision in a surgical procedure. The impact point may be in the form of an plate that is disposed at an end or each end of the anvil element.

The tool is further capable of regulating the frequency of the striker. By regulating the frequency of the striker, the tool may impart a greater total time-weighted percussive impact, while maintaining the same impact magnitude. This allows for the surgeon to control the cutting speed of the broach or chisel. For example, the surgeon may choose cutting at a taster rate (higher frequency impacting) during the bulk of the broach or chisel movement and then slow the cutting rate as the broach or chisel approaches a desired depth.

A user may firmly hold the tool by the handle portion and utilize light emitted by the LED to light up a work area and accurately position the broach, chisel, or other device on a desired location on the prosthesis or the implant. The reciprocating movement imparted on broach, chisel, or other device causes tapping of the implant and/or broach, chisel, or other device and thereby enables proper seating or removal of a prosthesis or implant into or out of an implant cavity, or controlled impacting of a broach, chisel, or other device to create or shape an implant cavity. The tool may also include a feedback system that warns the surgeon, when a bending or off-line orientation beyond a certain magnitude is detected at a broach, chisel, or other device/implant interface.

These together with other aspects of the present disclosure, along with the various features of novelty that characterize the present disclosure, is pointed out with particularity in the claims annexed hereto and forms a part of this present disclosure. For a better understanding of the present, disclosure, its operating advantages, and the specific objects attained by its uses, reference should be made to the accompanying drawing and descriptive matter in which there are illustrated exemplary embodiments of the present disclosure.

BRIEF DESCRIPTION OF THE DRAWINGS

The advantages and features of the present invention will become better understood with reference to the following detailed, description and claims taken in conjunction with the accompanying drawings, wherein like elements are identified with like symbols, and in which:

Like references numerals refer to like parts throughout the description of several views of the drawings.

DETAILED DESCRIPTION OF THE DISCLOSURE

The best mode for carrying out the present disclosure is presented in terms of its preferred embodiment, herein depicted in the accompanying figures. The preferred embodiments described herein detail for illustrative purposes are subject to many variations. It is understood that various omissions and substitutions of equivalents are contemplated as circumstances may suggest or render expedient, but are intended to cover the application or implementation without departing from the spirit or scope of the present disclosure.

The terms "a" and "an" herein do not denote a limitation of quantity, but rather denote the presence of at least one of the referenced items.

Referring now to FIGS. 1-6, the present disclosure provides an electric motor-driven orthopedic impacting tool with controlled percussive impacts. The tool includes the capability to perform single or multiple impacts as well as impacting of variable speeds, forces and frequencies. The impact force can be tuned to one of a variety of levels by setting the impact force electronically.

The tool includes a housing. The housing securely covers and holds a plurality of components of the tool. In an embodiment, the housing contains a motor, at least one reducing gear, a linear motion converter, a compression chamber, an impacting element (alternately referred to as a striker), a force or impact adjustment control means (hereinafter referred to as 'control means'), and an anvil element with a forward impact plate and a rearward impact plate (which impact plates may be part of the anvil, for example).

The tool further may include a handle portion with at least one hand grip for comfortable and secure holding of the tool while in use, a broach adapter, a battery, and a positional sensor, a directional sensor, and/or a torsion sensor. The tool may further comprise an lighting element such as an LED to provide light in the work area in which a user employs the tool. The broach adapter can be coupled to an anvil, of the anvil element for example, through a quick connect mechanism at the end of the tool that is directed at a patient when the tool is in use.

Figure 1:
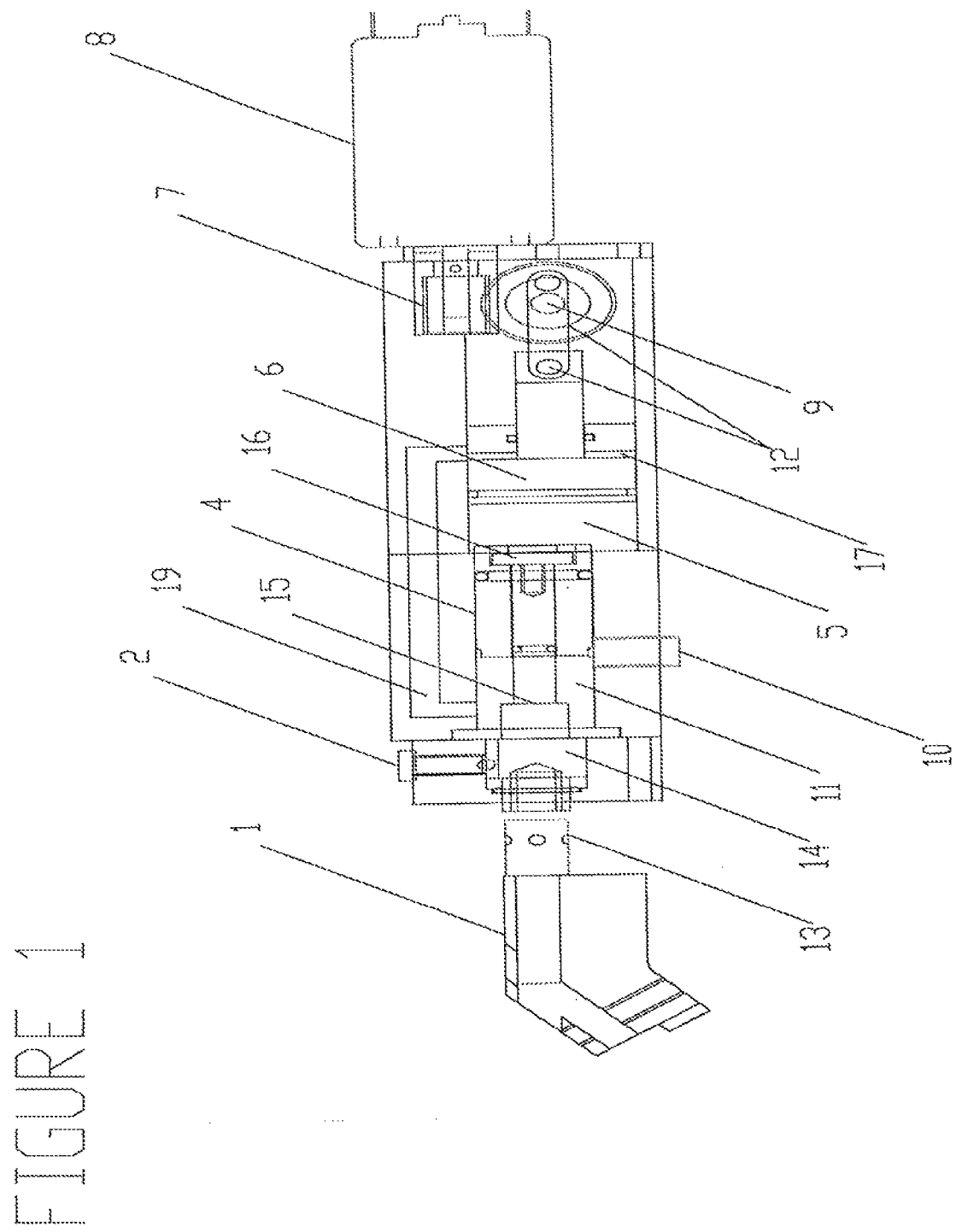
FIG. 1 shows a perspective view of an orthopedic impacting tool, in accordance with an exemplary embodiment of the present disclosure.
Figure 2:
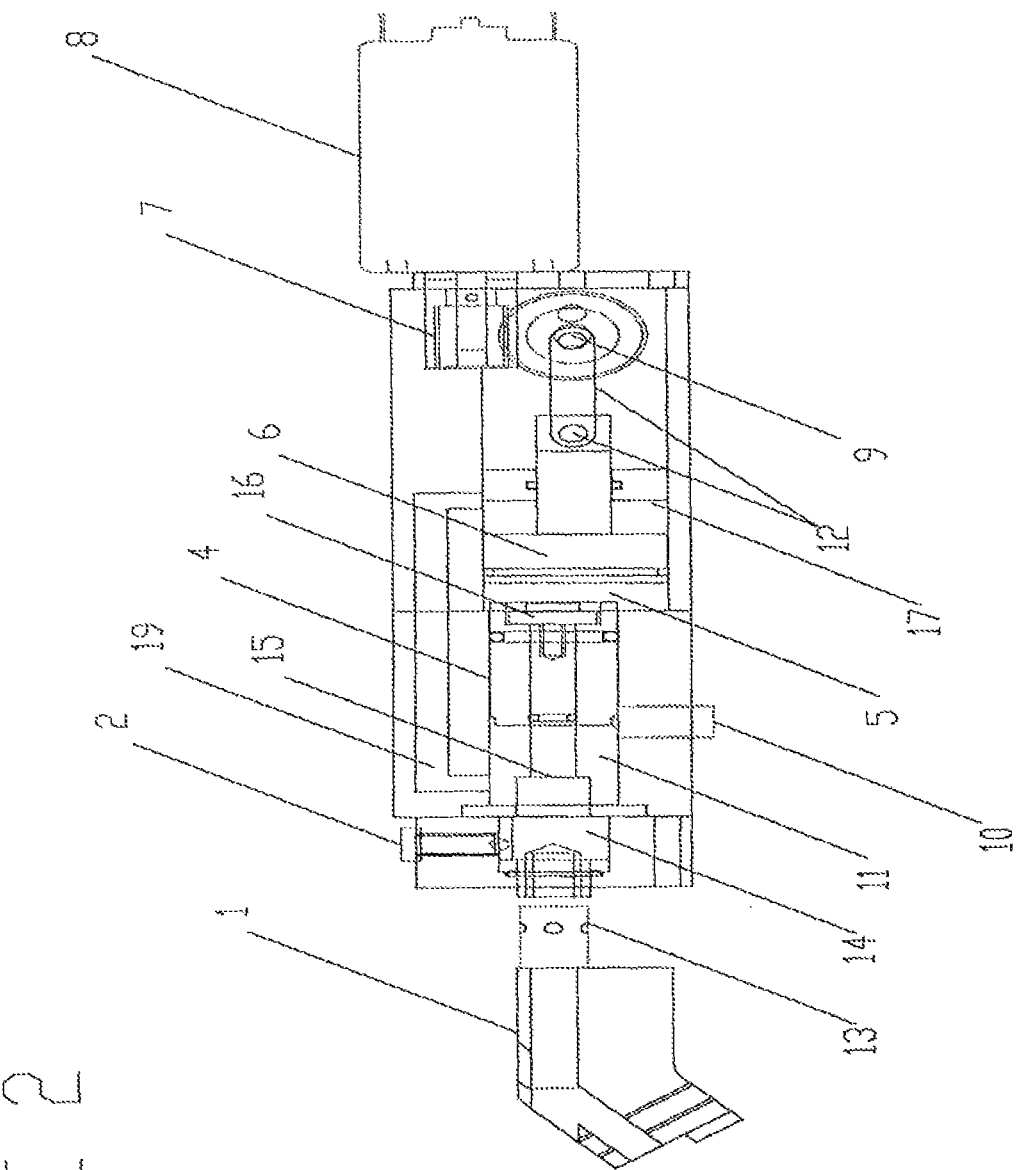
FIG. 2 shows a perspective view of a compression piston compressing air against a striker of an orthopedic impacting tool, in accordance with an exemplary embodiment of the present disclosure.
Figure 3:
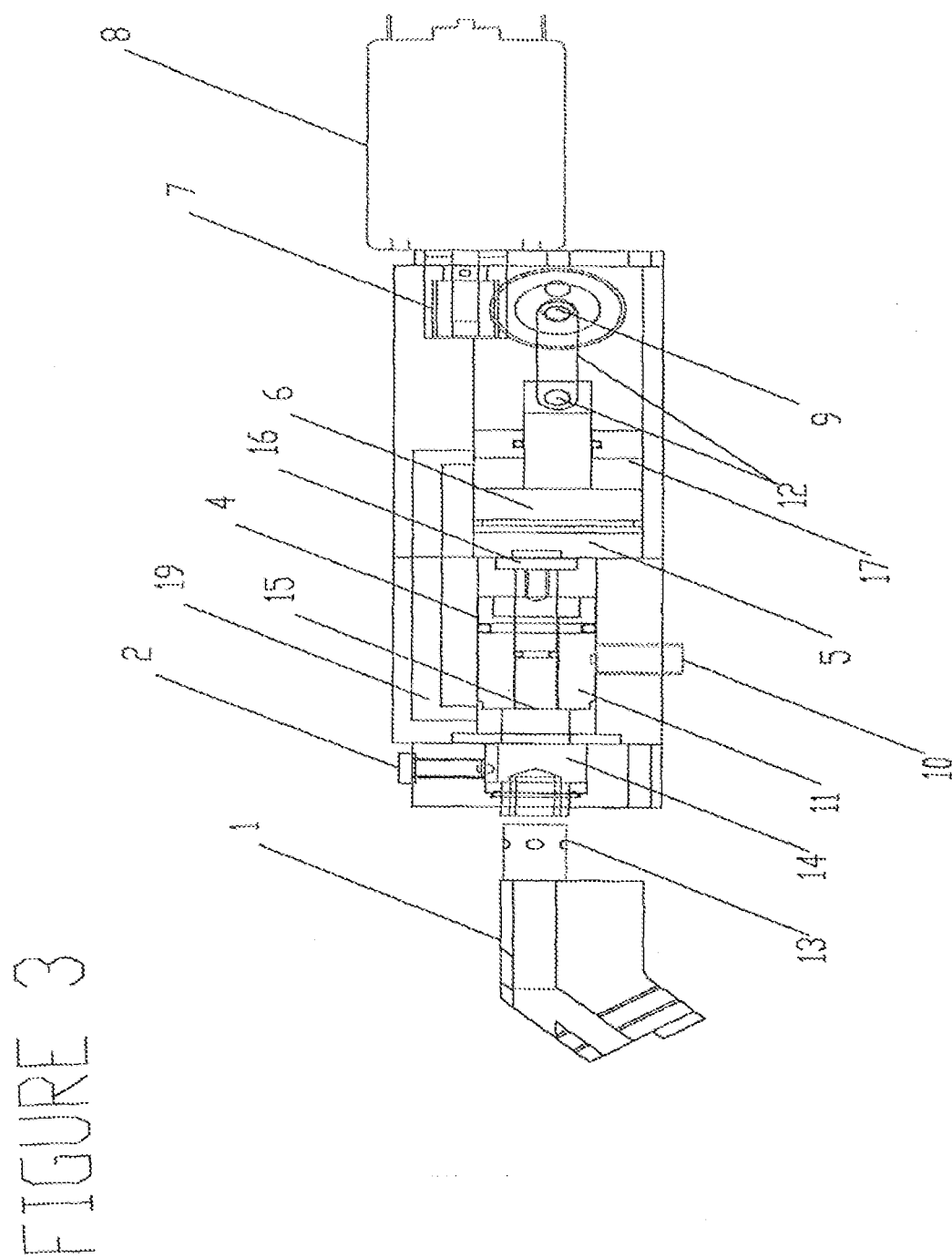
FIG. 3 shows a striker releasing and striking an anvil element, in accordance with an exemplary embodiment of the present disclosure.
Figure 4:
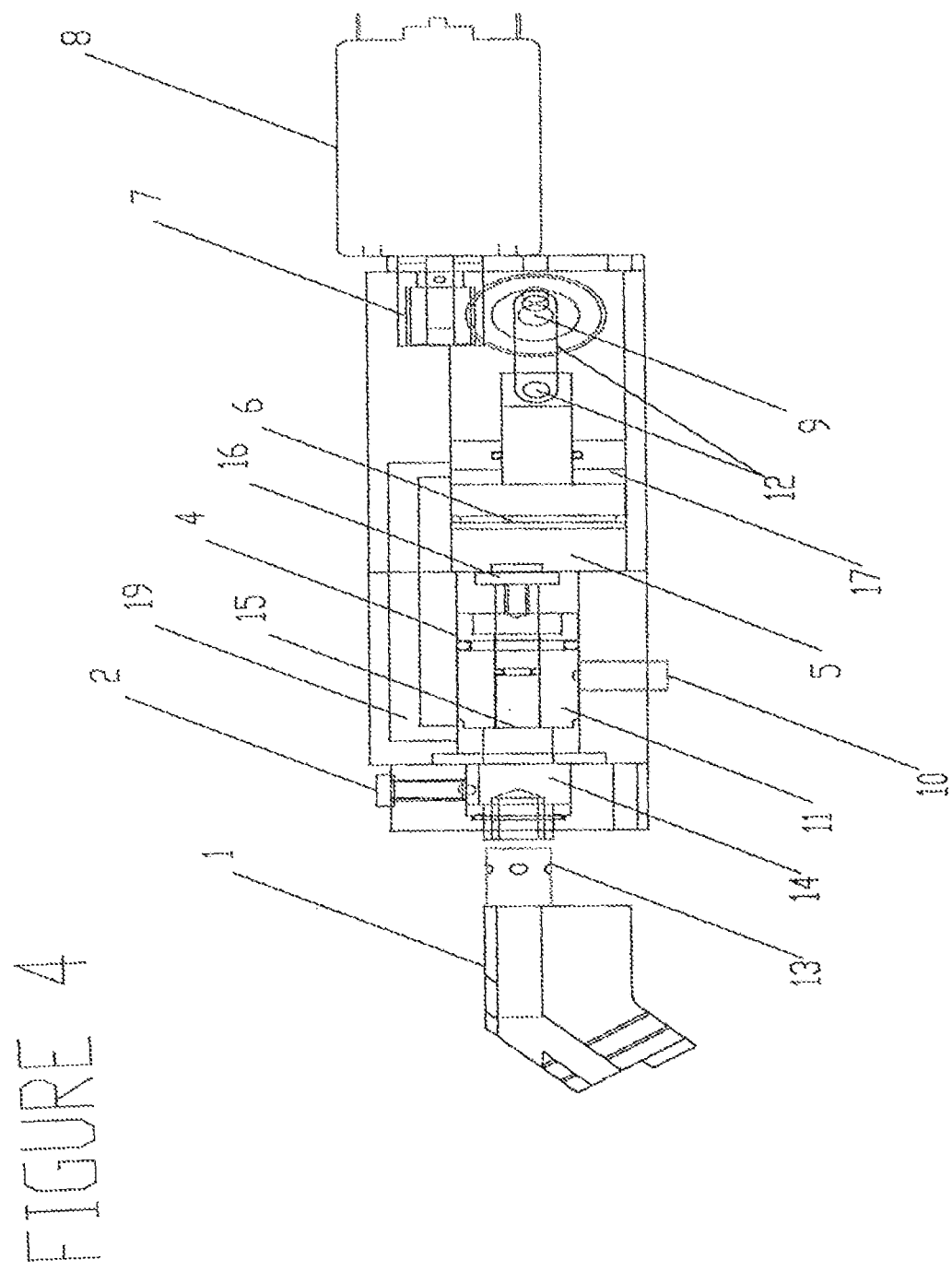
FIG. 4 shows a compression piston of an orthopedic impacting tool returning from a forward position and compressing air on the forward side of a striker, in accordance with an exemplary embodiment of the present disclosure.
Figure 5:
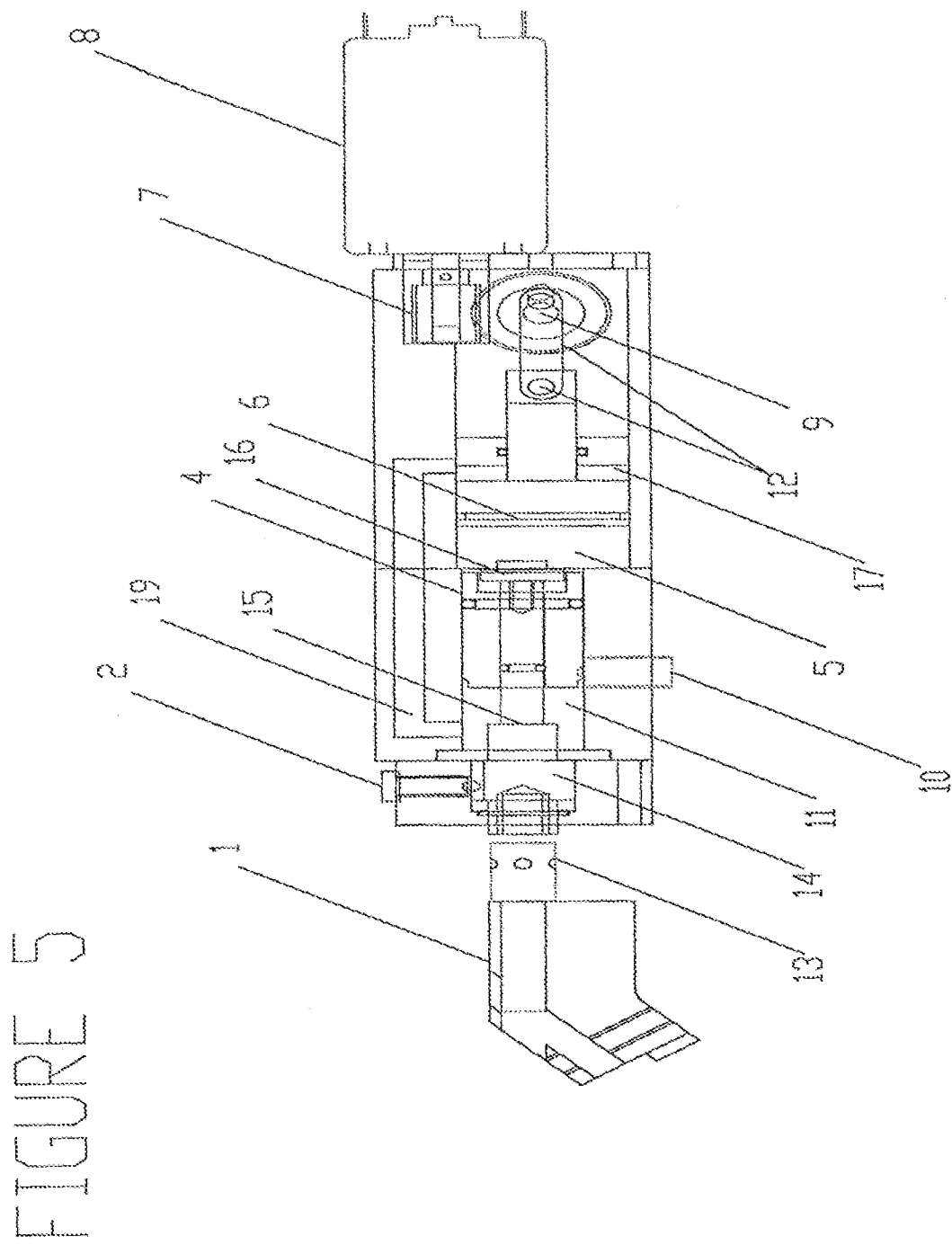
FIG. 5 shows a striker of an orthopedic impacting tool moving rearward, in accordance with an exemplary embodiment of the present disclosure.
Figure 6:
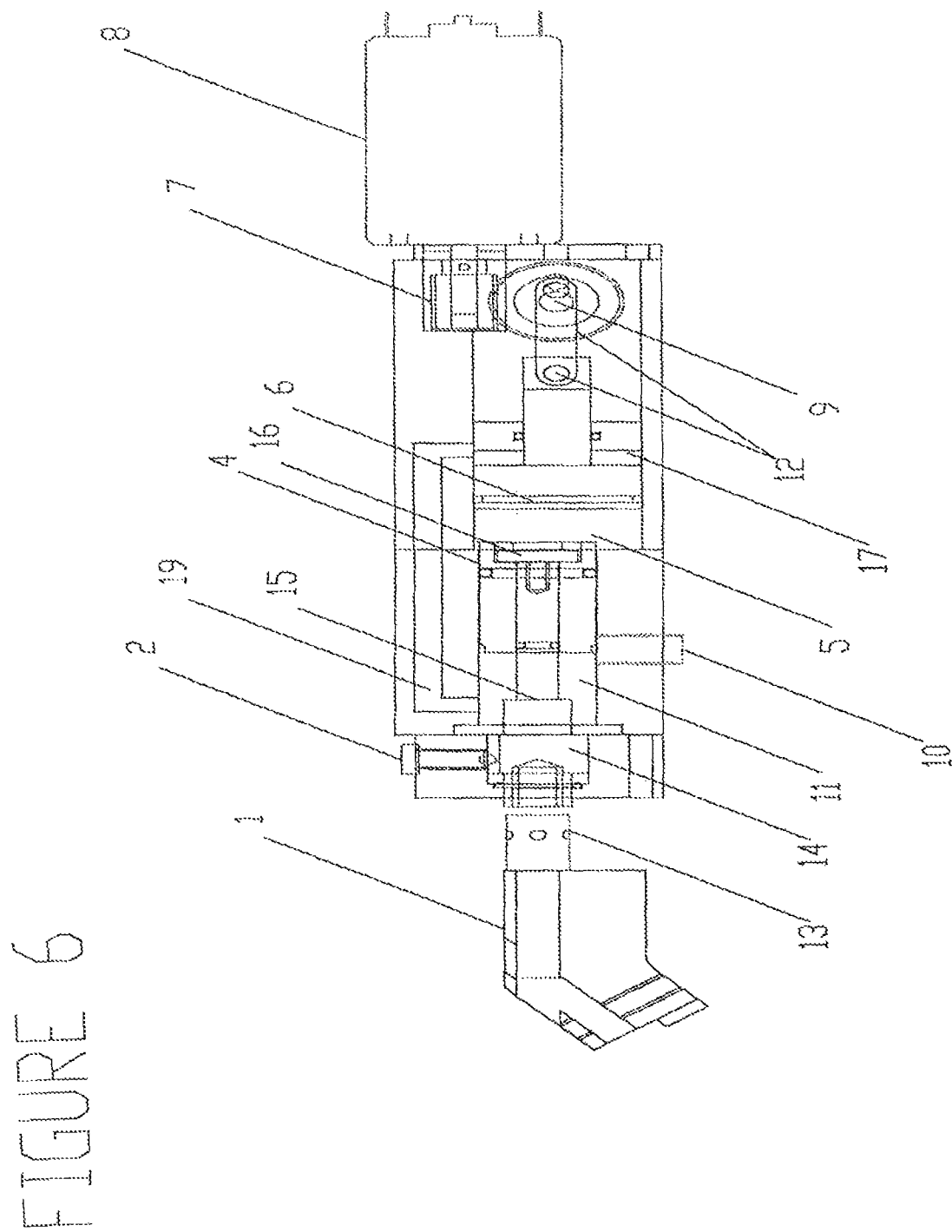
FIG. 6 shows a striker of an orthopedic impacting tool impacting a rear anvil impact plate, in accordance with an exemplary embodiment of the present disclosure.

In an embodiment, and referring now to FIG. 1, the linear motion converter comprises a slider crank mechanism 12, which slider crank is operatively coupled to the motor 8 and reducing gears 7 and 9. The tool further comprises an air chamber 5, 17 that accepts a compression piston 6 with a first end and a second end, which compression piston 6 is actuated by the linear motion converter 12. As the compression piston will have a smaller longitudinal dimension than the air chamber that contains the piston, it will be apparent that an air mass will be present at either end of the compression piston while the compression piston is within the air chamber. Hereinafter, the air mass disposed between the head of compression piston and the striker will be referred to as the "forward air chamber portion," or "forward air chamber" 5, and the air mass disposed between the end of the compression piston that is proximate to the linear motion converter and the motor of the tool will be referred to as the "rear air chamber portion," or "rear air chamber" 17.

In an embodiment of the present disclosure the motor of the tool, such as for example a voice coil motor, causes the linear motion converter to move the compression piston until sufficient pressure is built within the forward air chamber 5 that is disposed between the forward end of the compression piston and the rearward end of the striker 4 to overcome the inertia and frictional force that holds the striker 4 in a position. Once this sufficient pressure is reached, the force of the air pressure accelerates the striker 4, which striker 4 slides axially down a cavity internal to the tool housing and strikes the forward anvil impact plate 15. The resultant force is communicated through the anvil 14 that is proximate to the impact plate 15 and, optionally, through the broach adapter 1 (which adapter will be described in more detail below) to which a broach, chisel, or other device for seating or removing an implant, or prosthesis may be attached.

As the compression piston 6 continues through its stroke it moves towards the rear direction, compressing the air mass in the rear air chamber 17. This air mass may be communicated through art air passageway to the front side of the striker 4, creating a returning force on the striker 4, which returning force causes the striker 4 to move in a rear direction, i.e., a direction away from the point of impact of the striker the forward anvil impact plate 15. The striker continues to move until it impacts the rear anvil impact plate 16. Striking, the rear impact plate creates a rear directed force on the anvil 14. In the event that a broach adapter 1 is attached to the anvil 14, the force is communicated through the broach adapter 1 to which the broach, chisel, or other device fix seating or removing an implant, or prosthesis is attached. Thus in one complete cycle, a forward and rear directed impacting force can be applied on the broach, chisel, or other device, or implant/prosthesis.

In an embodiment, the compression piston preferably has a cavity on the head thereof, which cavity creates pressure during the return stroke of the piston, which pressure causes the front end of the striker to move away from the forward anvil impact plate impact the rearward point of impact of the anvil element. It will be apparent that the striker impacting the rear anvil impact plate will communicate a negative force to the front of the anvil (and broach, chisel, or other device), which negative force will move the broach, chisel, or other device away from the location of impact in a surgical area.

The slider crank embodiment of the tool facilitates controlled continuous impacting oldie striker and anvil. For such continuous impacting, after causing compression by the compression piston, the slider crank returns to the bottom of its stroke, which return releases pressure on the striker and, in the above-described embodiment wherein the piston comprises a cavity on the head thereof, may pressurize the front of the striker, causing the striker to return to its initial rest position.

For a single stroke, the linear motion converter (such as the slider crank described herein) will stop at or near the rear position, thus releasing the forward pressure on the striker and allowing the striker to return it to its starting position in readiness for another stroke. In this operational mode, a user may cause the tool to impact selectively (as opposed to repeatedly), thus allowing further control of the impacts and the creation or shaping of the surgical area, for example.

A positional sensor, coupled operatively to the control unit may be provided to assist in regulating a preferred positional cyclic operation of the linear motion converter. For example, the control unit ma cause the slider crank to come to rest at or near the fully back position in readiness to generate pressure for the next impact upon receiving a signal from the positional sensor that the slider crank has reached the bottom dead center position. In another embodiment, the control unit may be directly coupled to the linear motion converter for initiating and ceasing operation of the linear motion converter.

The control unit is further capable of operating the force control means for selectively tuning the amount of impact force per cycle. By controlling the impact force the tool can avoid damage caused by uncontrolled impacts or impacts of excessive force. For example, a user may reduce the impact setting in the case of an elderly patent with osteoporosis, or may increase the impact setting for more resilient or intact athletic bone structures.

The control unit may also control the force of impacting by modulating the speed of advancing (forward directional travel) and/or the speed of retraction (rearward directional travel) of the compression piston. It will be apparent that the modulation of speed of the compression piston will affect the buildup of pressure for forward and rearward directional travel of the striker. For example, where the speed of the forward direction of the piston is relatively high, and the speed of the rearward direction of the piston is relatively low, the velocity of the striker in the forward direction will be much higher, causing the imparted percussive impact of the striker to be greater in the forward direction of the piston and striker. This modulation of the speed of the piston in the forward and rearward direction allows a user to create a greater impacting force, when so desired (e.g., to create a surgical area) or a greater rearward force, to facilitate removing a broach, chisel, or other device from the surgical area, for example. In the instance where the forward and rear velocities are the same, the tool allows for bidirectional movement of the broach, chisel, or other device during operation, which creates a very efficient technique for machining the cavity.

The motor of the tool may be configured to assist particularly with such multidirectional impacting. In an embodiment, the motor may operate under pulse-width modulation for rearward striking and may operate under full or continuous speed for forward striking of the striker. In such operation, the broach, chisel, or other device attached to the tool may undergo near forward only motion, which operation will facilitate the creation of an implant seat. Alternatively, the motor may operate under pulse-width modulation for forward striking and may operate under full or continuous speed for rearward impacting, which operation can create an extraction motion useful for dislodging a broach, chisel, or other device that has become stuck or removing an implant.

In a further embodiment, the tool comprises a positional sensor, such as an anvil positional sensor that may be operatively coupled to the control unit of the striker of the tool. This positional sensor is capable of determining whether the operator is pushing or pulling on the tool. For instance, the sensor may determine such pushing, or pulling based upon the position of the broach-holding adapter or anvil. This determination can have the effect that when a user is exerting force on the tool in a particular direction the impacting of the striker is accordingly adjusted. For example, if the sensor determines that the user is pushing on the tool or is pushing the tool against an object, that sensor can cause the striker to impact in a forward direction. If the sensor determines that the user is pulling on the tool, that sensor may cause the striker to impact in a rearward direction or may cause a pulling force to be exerted on the striker by way of the cycling of the slider crank.

The tool may further comprise a lighting element, and, in an embodiment, the lighting element may comprise an LED arrangement, which lighting element may be capable of illuminating a user's work area. In an embodiment, the LED may be disposed on the housing of the tool and may be oriented toward a patient's body or surgical cavity.

The tool may further comprise a plate or other flat surface at the end of the tool that is distal to the surgical area, which plate may allow a user to apply selective manual pressure on a broach, chisel or other device, or a surgical implant as dictated by surgical or physical conditions. For instance, if a broach is firmly lodged within a cavity such that the operation of the tool would not remove the broach, the user may manually tap on the plate to dislodge the broach.

The tool may further comprise a torsion sensor, which torsion sensor may be capable of determining a lateral or deviating force or movement of the tool, such that if the tool is sensed to deviate from a pre-determined magnitude at the broach/implant interface, a signal may emit to notify the user of such deviation. In this manner and otherwise, the tool facilitates consistent axial broaching and implant seating.

In a further embodiment, the broach adapter may comprise a parallel 4-bar arrangement. In this embodiment, the adapter may receive a broach for anterior or posterior joint replacement. The parallel 4-bar mechanism of the adapter may facilitate receiving and orienting the broach in a variety of positions, such as in a centered position, or in an offset left or right position. The adapter will maintain the broach in an orientation that is parallel or co-linear to the body of the tool and the striker. The broach adapter may also comprise clamps, a vice, or any other fastener that may securely hold the broach, chisel, or other device, during operation of the tool.

The tool may further comprise handgrips disposed on the housing of the tool, which handgrips may include a rubberized or other tacky coating removably disposed thereon. Such coating facilitates comfortable operation of the tool and improves the user's hold on the tool for increased control thereof and reduced fatigue during operation of the tool.

In use, a user such as a surgeon firmly holds the tool by the handle grip or grips and utilizes light emitted by the LED to illuminate a work area and accurately position a broach, chisel or other device that has been attached to the tool on a desired location on the prosthesis or implant. The reciprocating movement imparted by the tool upon the broach, chisel or other device causes tapping of the implant and thereby enables proper seating, or removal of the prosthesis or the implant into or out of an implant cavity. The warning system may alert the user in the event that a bending moment above a certain magnitude is detected at a broach (or chisel or other device)/implant interface.

The tool disclosed herein provides various advantages over the prior art. It facilitates controlled impacting, at a surgical site, which minimizes unnecessary damage to a patient's body and which allows precise shaping of a implant or prosthesis seat. The tool also allows the user to modulate the direction and force of impacts, which improves the user's ability to manipulate the tool. The force control adjustment of the impact settings allows a user to set the force of impact according to a particular bone type or other profile of a patient. The tool thereby enables proper seating or removal of the prosthesis or the implant into or out of an implant cavity.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the disclosure and various embodiments with various modifications as are suited to the particular use contemplated.

What is claimed is:

1. An orthopedic impacting tool for striking an object, the tool comprising:
   a motor based drive assembly;
   a compression piston operatively coupled to said motor based drive assembly, said compression piston having a first end and a second end;
   an air chamber, said air chamber comprising a forward portion and a rear portion, wherein
      said forward portion is proximate to said first end of said compression piston, and
      said rear portion is proximate to said second end of said compression piston;
   an impacting element;
   a control unit;
   an anvil element with a front face and a rear face, said anvil element adapted to accept a portion of a broach adapter,
      the broach adapter capable of holding a broach, chisel, reamer, or other surgical implement,
      said broach adapter operatively coupled to said anvil element and being proximate to said first face of the anvil element and distal to said second face of said anvil element; and
   a hand grip;
   wherein said control unit directs said motor based drive assembly to cause said compression piston to move and compress air within said front portion of said air chamber or compress air within said rear portion of said air chamber, and wherein
      said impacting element cyclically impacts said front face of said anvil element upon application of compressed air from the front portion of said air chamber, and
      wherein said impacting element cyclically impacts said rear face of said anvil element upon application of compressed air from the rear portion of said air chamber,
      such that the impacting element is capable of imparting a force upon the broach adapter in at least one direction.

2. The tool of claim 1, wherein said motor based drive assembly includes a linear motion converter which comprises a slider crank mechanism.

3. The tool of claim 2, wherein said motor based drive assembly comprises a voice coil motor.

4. The tool of claim 1, wherein the control unit allows for single percussive impacting.

5. The tool of claim 1, wherein said tool further comprises a lighting element disposed on an exterior surface of the tool, said lighting element operatively coupled to the control unit.

6. The tool of claim 1, wherein a velocity of said impacting element is controlled by a speed at which the air is compressed or decompressed.

7. The tool of claim 1, wherein the tool comprises a positional sensor that is operatively coupled to one of the control unit of the tool or the motor based drive assembly of the tool,
   the positional sensor to determine whether the tool is being pushed toward the object or pulled away from the object,
   which the positional sensor causes said control unit or motor based drive assembly of the tool to direct the impacting element to impart a greater force upon said front face of said anvil element and a lesser force on said rear face of said anvil element upon sensing that the tool is being pushed toward the object, and
   which the positional sensor causes said control unit or motor based drive assembly of the tool to direct the impacting element to impart the lesser force upon said front face of said anvil element and the greater force on said rear face of said anvil element upon sensing that the tool is being pulled away from the object.

8. The tool of claim 1, wherein said tool comprises a torsion sensor, which torsion sensor is capable of determining a lateral movement of the tool and which sensor is capable of signaling such movement.

9. The tool of claim 1, wherein said broach adapter has an adjustment to offset the attached broach, chisel, reamer, or other surgical implement from a central axis of the tool while maintaining a parallel orientation of the broach, chisel reamer, or other surgical implement with respect to the central axis of the tool.

10. The tool of claim 1, wherein said broach adapter comprises a parallel four-bar mechanism.

* * * * *